(12) United States Patent
Grau et al.

(10) Patent No.: US 8,048,683 B2
(45) Date of Patent: Nov. 1, 2011

(54) INSECT REPELLENT AND PROCESS FOR IDENTIFYING OTHER INSECT REPELLENT MOLECULES

(75) Inventors: Yves Grau, Saint Gely du Fesc (FR); Christian Mitri, Paris Cedex (FR); Marie-Laure Parmentier, Montpellier (FR)

(73) Assignees: Centre National de la Recherche Scientifique, Paris (FR); Universite de Montpellier I, Montpellier (FR)

( * ) Notice: Subject to any disclaimer, the term of this patent is extended or adjusted under 35 U.S.C. 154(b) by 69 days.

(21) Appl. No.: 12/300,623

(22) PCT Filed: May 14, 2007

(86) PCT No.: PCT/FR2007/000813
§ 371 (c)(1), (2), (4) Date: Mar. 18, 2009

(87) PCT Pub. No.: WO2007/132090
PCT Pub. Date: Nov. 22, 2007

(65) Prior Publication Data
US 2009/0220428 A1 Sep. 3, 2009

(30) Foreign Application Priority Data
May 15, 2006 (FR) .................................. 06 04292

(51) Int. Cl.
*G01N 33/566* (2006.01)
*C07K 14/705* (2006.01)

(52) U.S. Cl. ............................ 436/501; 435/7.1; 435/7.2

(58) Field of Classification Search ........................ None
See application file for complete search history.

(56) References Cited

U.S. PATENT DOCUMENTS
2003/0092124 A1 5/2003 Cravchik

OTHER PUBLICATIONS

Mitri, Christian et al. "Divergent Evolution in Metabotropic Glutamate Receptors" The Journal of Biological Chemistry, 279: 9313-9320, 2004.
Gasparini, Fabrizio et al "Allosteric modulators of group I metabotropic glutamate receptors: novel subtype-selective ligands and therapeutic perspectives" Current Opinion in Pharmacology, 2: 43-49, 2002.
Taniura, Hideo et al. "A Metabotropic Glutamate Receptor Family Gene in Dictyostelium discoideum" The Journal of Biological Chemistry and Molecular Biology, Inc., 281: 12336-12343, 2006.
Hoao, Chi "Comparative study on insecticidal activity of L-canavanine and carbonfuran against *Pieris brassicae* L." Database Caplus, Chemical Abstracts Service, 1998.
Rosenthal, Gerald et al. "Effect of Long-chained Esters on the Insecticidal Properties of L-Canavanine" J. Agric. Food Chem., 46: 296-299, 1998.
Database Zregistry, Chemical Abstracts Service, 1984, Database accession No. 60890-85-9.
Database Zregistry, Chemical Abstracts Service, 1984, Database accession No. 50472-71-4.
Database Zregistry, Chemical Abstracts Service, 1984, Database accession No. 27648-09-5.
Qyitt, P. et al. "Die Synthese optisch aktiver N-Monomethyl-Aminosauren" 327-333, 1963.
Pundak, Shlomo et al. "Synthesis of Guanidino-N-alkylarginines by the use of Polymeric Pseudoureas" J. Org. Chem., 46: 808-809, 1981.

*Primary Examiner* — John Ulm
(74) *Attorney, Agent, or Firm* — Morgan, Lewis & Bockius LLP

(57) ABSTRACT

This invention is based on the identification of the role played by the receptor mX on certain insects through the behavior evinced in the taste sensory reactions of these insects. The invention addresses the use of the modulators on the mX receptor, such as L-canavanine and/or a mix of arginine and calcium and/or N-methyl-L-arginine (NMA) which are used to prepare a compound with repellent or attractive qualities with regard to certain insects. The invention also concerns the use of an mX insect receptor as a target for the identification of repellent substances regarding at least some insects.

9 Claims, 6 Drawing Sheets

INSECT REPELLENT AND PROCESS FOR IDENTIFYING OTHER INSECT REPELLENT MOLECULES

RELATED APPLICATIONS

The present application is a U.S. National Phase Application of International Application PCT/FR2007/000813, filed May 14, 2007, which claims the benefit of French Application No. 0604292, filed May 15, 2006, all of which are herein incorporated by reference in their entirety.

The present invention relates to the field of insect control, and more particularly to the field of insect-repellent products.

At the current time, insecticidal or insect-repellent molecules are used to control insect pests. However, two major problems have emerged and have become stronger over the last few years. The first problem is related to the limited effectiveness of these molecules over time, due to the great ability of insects to adapt. Specifically, insects rapidly develop resistances with respect to the insecticidal or insect-repellent molecules, through mutations of the molecular target, resulting in a decrease in, or even a loss of, affinity of these molecules for their target. The second problem is related to the toxicity of these molecules with respect to other organisms, such as mammals, and in particular humans. The toxicity of these insecticidal or insect-repellent molecules is mainly due to the fact that their targets are conserved in mammals.

Insect pests are essentially crop-ravaging pests and also vectors of certain diseases which cause the death of several million individuals per year. Insect control is in particular an essential tool in the prevention of vector-borne diseases. For example, for certain diseases against which no effective vaccine is available (malaria, dengue, chikungunya), individual protection against mosquito bites makes it possible to protect oneself; the use of repellents coated onto the exposed skin is, in this context, a widely used means of protection.

Several synthetic and natural repellents exist on the market. DEET (N,N-diethyl-3-methylbenzamide) is the reference synthetic repellent. However, it has the drawback of being partly eliminated by evaporation, but especially by dermal absorption. Another drawback of DEET is that it damages plastics (eye glasses, bracelets, etc). The repellents of natural origin (such as citronella) provide very short-term protection, often less than one hour (Fradin and Day, 2002).

Today, there therefore exists a considerable need to find new insect-repellent molecules which are stable over time and nontoxic for mammals, in particular for humans.

In this context, the inventors have demonstrated a repellent effect of the amino acid L-canavanine in *drosophila*. They have demonstrated that this repellent effect involves a heptahelical receptor which they had previously identified (Mitri, Parmentier et al., 2004). This receptor, called "mX receptor", or "mXR", is a G-protein-coupled receptor, homologous to the metabotropic glutamate receptors (G-protein-coupled receptor family C) (Mitri et al., 2004). The mX receptor is characterized by a particular consensus sequence of residues in the pocket for binding of the ligand (not identified), which consensus sequence differs from that of metabotropic glutamate receptors (Mitri et al., 2004). The inventors have identified this receptor in several insects (currently the *drosophilas Drosophila melanogaster, Drosophila pseudoobscura* and *Drosophila virilis*, the mosquitoes *Anopheles gambiae* and *Aedes aegypti*, the bee *Apis mellifera* and the butterfly *Bombyx mori*) and shown that it does not exist in the genome of the nematode *C. elegans*, or in the vertebrate genome (zebrafish, mouse, human). There exists lust one gene encoding an mX receptor in the species in which it has been identified. To date, this receptor therefore appears to be specific for insects.

Despite its repellent effect against *drosophila* and probably other insects, L-canavanine does not appear to be a molecule that can be directly used as a repellent, because of its toxicity. It is known that L-canavanine (L-2-amino-4-(guanidinooxy) butyric acid), synthesized by more than 1200 species of leguminous plants, is a powerful insecticide. Specifically, in many insect species treated with L-canavanine, it has been described that this amino acid, which is a nonprotein amino acid in the leguminous plants which synthesize it, can be incorporated into the proteins synthesized de novo by arginyl-tRNA synthetase, in place of arginine (Rosenthal 1977; Rosenthal 2001). This incorporation gives defective proteins which have abnormal three-dimensional structures, gradually resulting in sterility or in death. These toxic effects of L-canavanine, mainly described in insects during larval development, have been found in a large number of species, from viruses to human (review by Rosenthal, 1977).

The inventors have now identified the natural ligand of the insect mX receptor. They have shown that this natural ligand, namely L-arginine associated with calcium, is insect repellent. In addition to the fact that the arginine associated with calcium can be used as a repellent, these results show that the mX receptor constitutes a particularly advantageous target candidate for identifying new repellent substances or molecules against certain insects, since it appears that other mX receptor ligands will themselves also have a repellent effect.

The present invention therefore relates, firstly, to the use of an mX receptor activator as a repellent for certain insects, and more particularly to the use of such a receptor for the preparation of a composition that is repellent for at least certain insects. As seen above, the inventors have, to date, identified the mX receptor in the *drosophila Drosophila melanogaster*, the mosquito *Anopheles gambiae*, the bee *Apis mellifera* and the butterfly *Bombyx mori* and also in the genome of other *drosophila* species (*Drosophila* pseudoobscura (chromosome 3), *Drosophila virilis* (scaffold 12875)) and in a sequence of an insect pest, the mosquito *Aedes aegypti* (AAGE02017413.1), which is a vector for dengue. In addition, they have not identified any insect lacking this receptor, which appears to be particularly-conserved in insects. An activator of the mX receptor of *drosophila* is therefore probably repellent for any insect. Dipteran pests constitute an essential target of the repellent compositions according to the invention, since the mX receptor is found in all the dipteran genomes currently sequenced: mention may in particular be made of sandflies, which are small dipterans of which the female is hematophagus and transmits cutaneous leishmaniasis and visceral leishmaniasis (an emerging disease in southern Europe, in particular in leishmaniasis-HIV/AIDS coinfection), the tsetse fly, a vector for sleeping sickness, and mosquitoes of the *Aedes* genus, which are vectors for yellow fever, chikungunya and dengue. Among the insects targeted according to the invention, mention may also be made of bees, butterflies, locusts, wasps, etc.

The expression "mX receptor modulator" is, of course, intended to mean any ligand capable of activating mXR (i.e. an mX receptor activator), but also any ligand which is an antagonist of the mX receptor (i.e. an mX receptor inhibitor). In fact, it has been shown that the gustatory response to certain amine acids studied, such as methionine and valine, may depend on the insect species studied, ranging from stimulant to repellent (Chapman 2003). The antagonists make it possible to inhibit mX receptor activation in the case where the arginine and calcium contained in the natural nutritive medium trigger an attractive behavior in certain insect species. Another category of mX receptor modulators consists of the allosteric regulators—positive or negative—of this receptor. Allosteric regulators have been described for mGlu receptors (Gasparini, Kuhn et al., 2002); due to the great homology between these receptors and mXRs, the same mechanism of regulation (via binding to the transmembrane domain) certainly exists for mX receptors.

According to one preferred embodiment of the present invention, the mX receptor activator is a mixture of arginine and of calcium. The association of L-arginine and calcium in fact constitutes a natural mXR activator, which has several advantages, among which mention may be made of the stability of the compounds and the probable lack of toxicity thereof. These properties make it possible to envision all types of possible uses, depending on the field of application (anti-insect cosmetology, disinfection of premises, agrochemistry, etc). A composition according to the invention may therefore be in the form of a cream, a lotion or a spray for topical application (in particular for preventing mosquito bites), or in the form of an aerosol to be given off or of particles to be dissolved in water for treating large surfaces, for example for protecting dwellings or crops. The arginine and the calcium may be provided in the mixture in various forms known to those skilled in the art. For example, the arginine may be in the form of L-arginine directly and/or of arginine salt; the calcium may also be in the form of a salt, such as calcium chloride, calcium carbonate or calcium fluoride.

In one preferred use according to the invention, the concentrations of arginine and of calcium in the composition are greater than 1 mM, and preferably at least 10 mM. More preferably, the concentrations of arginine and of calcium are between 15 and 100 mM, preferably between 20 and 50 mM. Advantageously, the concentration of calcium is approximately double that of the arginine.

The present invention also relates to paints or other coatings, comprising L-canavanine and/or arginine and calcium, in order to confer insect-repellent properties thereon. An article, in particular a textile article (mosquito net, article of clothing, or the like) impregnated with a composition as described above, is also an integral part of the present invention.

The present invention also relates to a method for repelling certain insects, in which surfaces are treated with a mixture of arginine and calcium.

In certain cases it may be advantageous net to repel the insects, bur to attract them. For example, it is useful to attract insect pests into traps. It may also be useful to attract, onto crops, beneficial insects which will promote pollination of the plants or which will destroy insect pests. For the reasons explained above, an action on the mX receptor may, depending on the insects and depending on whether it is an activating or inhibitory action on the receptor, lead to repulsion or, on the contrary, attraction of the insects in question.

The present invention therefore also relates to a composition that is attractive for certain insects, characterized in that it comprises at least one mX receptor modulator. In one preferred embodiment of this aspect of the invention, the modulator is an mX receptor inhibitor, such as, for example, N-methyl-L-arginine (NMA), advantageously present at a concentration of greater than 10 mM, preferably greater than 20 mM. The use of N-methyl-L-arginine (NMA), for the preparation of an insecticidal composition that attracts certain insects, is therefore also part of the invention.

The attracting compositions according to the invention may also comprise an insecticide, in addition to an mX receptor modulator, for example for preparing insect traps. The mX receptor modulators, and in particular the inhibitors such as NMA, may in fact be advantageously used in insect-pest traps, in combination with an attractant with a non-local effect (as appropriate, light, $CO_2$, heat, odor, etc) and an insecticide. The action of the mX receptor ligand may be directly attractive, but its effect may also be related to a deinhibition, in an insect species, of a feeding behavior with respect to a medium, which behavior would be negatively regulated by another compound (in particular, an insecticide) contained in the medium.

Another aspect of the present invention concerns the use of L-canavanine and/or of a mixture of arginine and calcium and/or of NMA, as control (s) in a screening test for identifying mX receptor ligands. L-Canavanine and/or a mixture of arginine and calcium may be used as positive controls for binding to the mX receptor in any type of screening method for identifying mX receptor agonist ligands, whether this involves screening in silico by modeling, in vitro (for example, in a test as described in the experimental section below) or in vivo (for example, in a gustatory choice test, as also described in the experimental section).

Another particularly important aspect of the invention is the use of an insect mX receptor as a target for identifying substances that are repellent for at least certain insects. The term "substances" is intended to mean herein and in the subsequent text, not only the molecules present in the molecular databases—for example, more than three million molecules can be screened in silica for their binding to the mX receptor pocket—but also more complex substances, such as cell extracts, plant extracts, etc., which can be tested in vitro or in vivo.

In the context of the present invention, a screening method for identifying a substance that is repellent for at least one insect species preferably comprises a step of selecting the substances that bind to the mX receptor of said insect. Thus, the search for repellent molecules for the mosquitoes will preferably be carried out by searching for ligands of the AgmXR receptor of *Anopheles gambiae*. However, the very high degree of homology of the mX receptor between one insect species and another makes it possible to assume that a substance that binds to the AgmXR receptor and that is repellent for mosquitoes, will also have a repellent effect on other insects, such as wasps, locusts, etc.

According to one preferred embodiment, a screening method according to the invention comprises a step of selecting the substances that activate or inhibit the mX receptor. As seen above, several methods of activation of mXRs may exist, and a modulator may be a competitive ligand or an allosteric regulator.

The screening method according to the invention may be carried out by using any insect mX receptor. By way of examples of receptors that can be used, mention may be made of the DmXR receptor *Drosophila melanogaster*, of *Drosophila pseudoobscura* or of *Drosophila virilis*, the AgmXR receptor of *Anopheles gambiae*, the mXR receptor of *Aedes aegypti*, the HBraXR receptor of *Apis mellibera* and the mXR receptor of *Bombyx mori*. The key residues forming the L-canavanine- and L-arginine-binding pocket are identical in the four insect species mentioned above; the activators of the receptor of *drosophila*, for example, will therefore very probably be activators of the mX receptor of many insects.

A screening method according to the invention preferably comprises at least one step of in vitro screening, by bringing the test substances into contact with the mX receptor chosen. This in vitro screening step may be carried out on cells in culture which express the mX receptor, whether they are insect cells naturally expressing said receptor, or cells transfected with an expression vector for this receptor and which express it either transitorily or, preferably, stably. An example of an in vitro test that can be used in the context of the invention is described in the article by Mitri et al., above, and in the experimental section below. The use of a cell transformed with an expression vector for the mX receptor, for identifying substances that are repellent for at least certain insects, is also part of the present invention.

According to one preferred embodiment of the method of the invention, the method comprises a step of determining, in vivo, the repellent effect of the substances selected in vitro. This step of determining, in vivo, the repellent effect may comprise or consist of a gustatory choice test. An example of a gustatory choice test, on *drosophilas*, is described in the experimental section below.

In addition, a screening method according to the invention may comprise, upstream of the in vitro screening step, a step of screening test molecules in silico.

According to one particular embodiment of the screening method above, an additional step is added in order to determine whether the repellent action of a substance selected is exclusively linked to the binding of said substance to the mX receptor. This step consists of a test carried out on at least one mX receptor functional loss mutant, for example on flies in which the mX gene has been rendered nonfunctional, or the expression of said gene has been inhibited.

In addition to the arrangements above, the invention also comprises other arrangements which will emerge from the experimental examples below, which refer to the attached figures in which.

Figure 3:
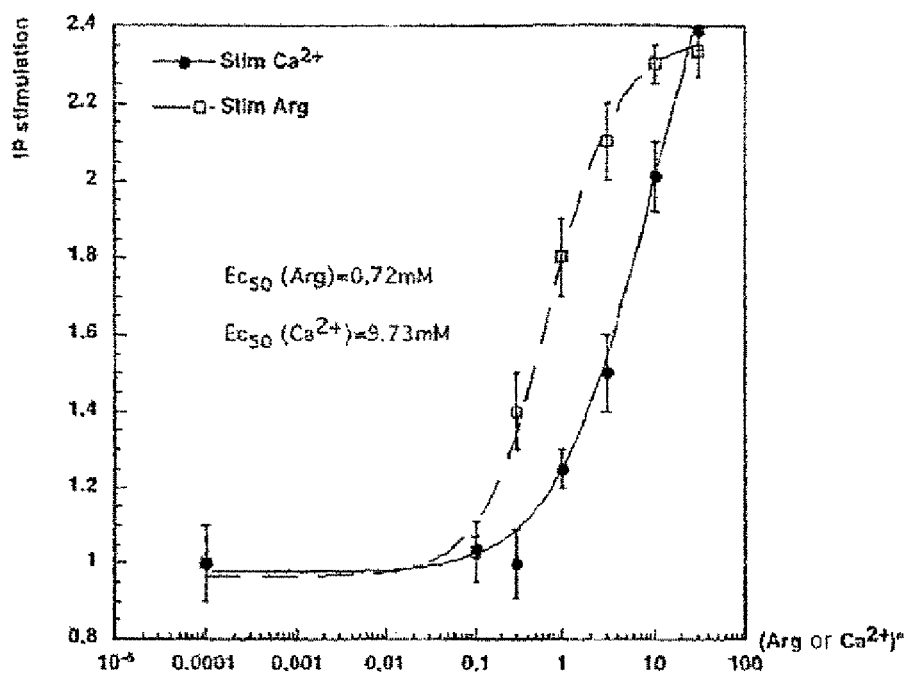

FIG. 3 gives the result of pharmacological tests showing the dose-response effect of arginine in the presence of 10 mM of calcium (dashed curve) and of calcium in the presence of 10 mM of arginine (solid curve; on HEK cells transfected with Gαqi/9 and DmXR.

Figure 4:
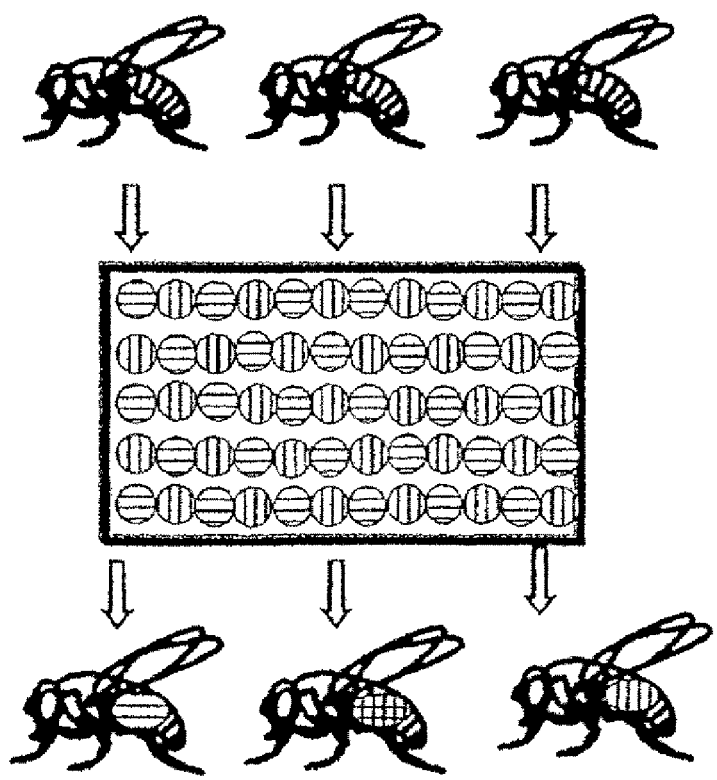

FIG. 4 gives a scheme of the behavioral test carried out in order to measure the chemosensory effect of the DmX receptor ligands. The horizontal stripes symbolize erioglaucine (blue dye), whereas the vertical stripes symbolize sulforhodamine (red dye). When the flies have ingested the two solutions, the content of their digestive tube is violet, which is here shown schematically by a grid pattern.

Figure 5A:
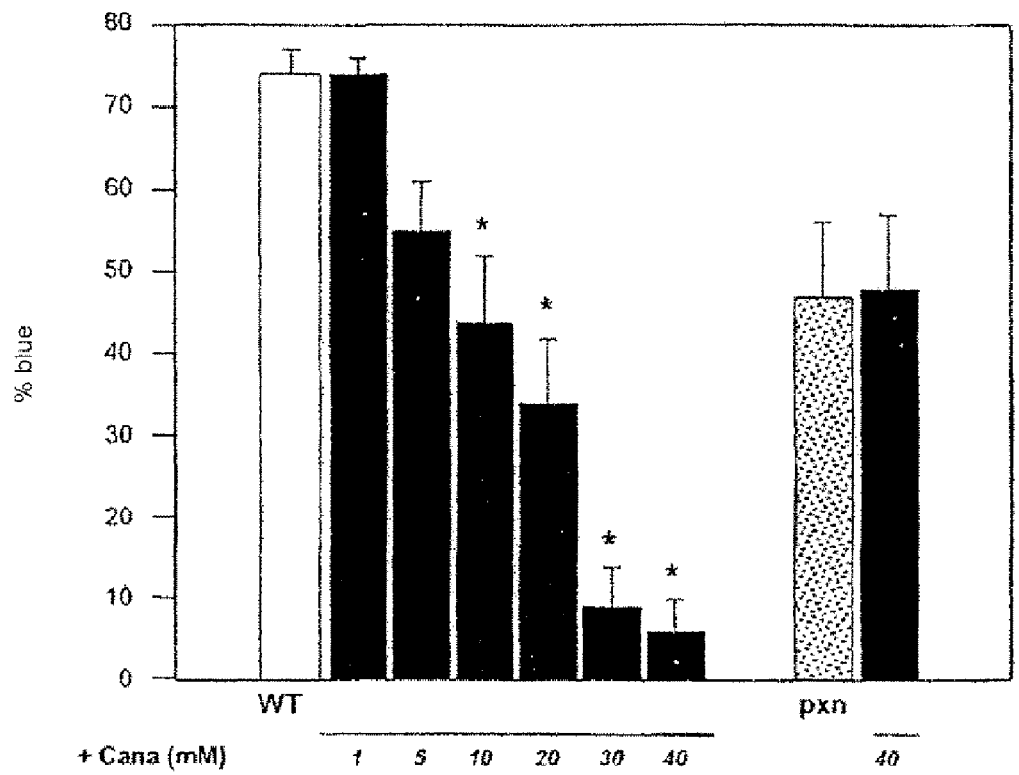
Figure 5B:
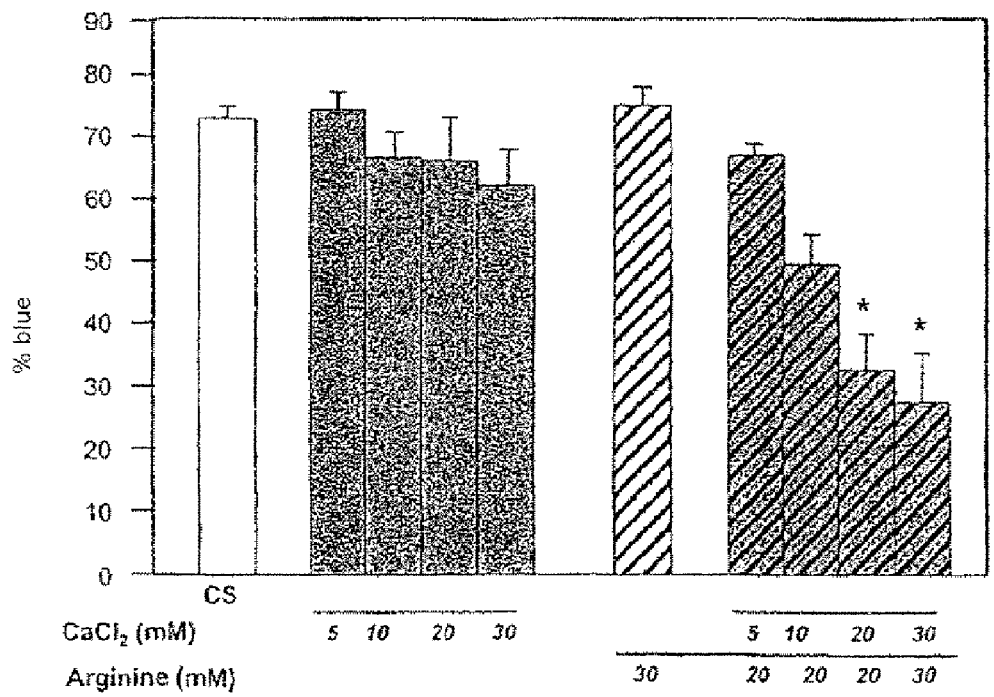

FIG. 5 shows the result of the behavioral tests carried out. Each situation is represented by the percentage of flies having eaten blue medium (% blue=number of blue abdomens/(number of blue abdomens+number of two-colored abdomens+number of red abdomens)×100). *=P<0.01. FIG. 5A shows the result of the behavioral tests carried out on wild-type *drosophilas* (CS) and on mutant *drosophilas* (pox-neuro70) (n=10). FIG. 5B gives the result of the behavioral tests carried out on wild-type *drosophilas* (n=6).

Figure 6:
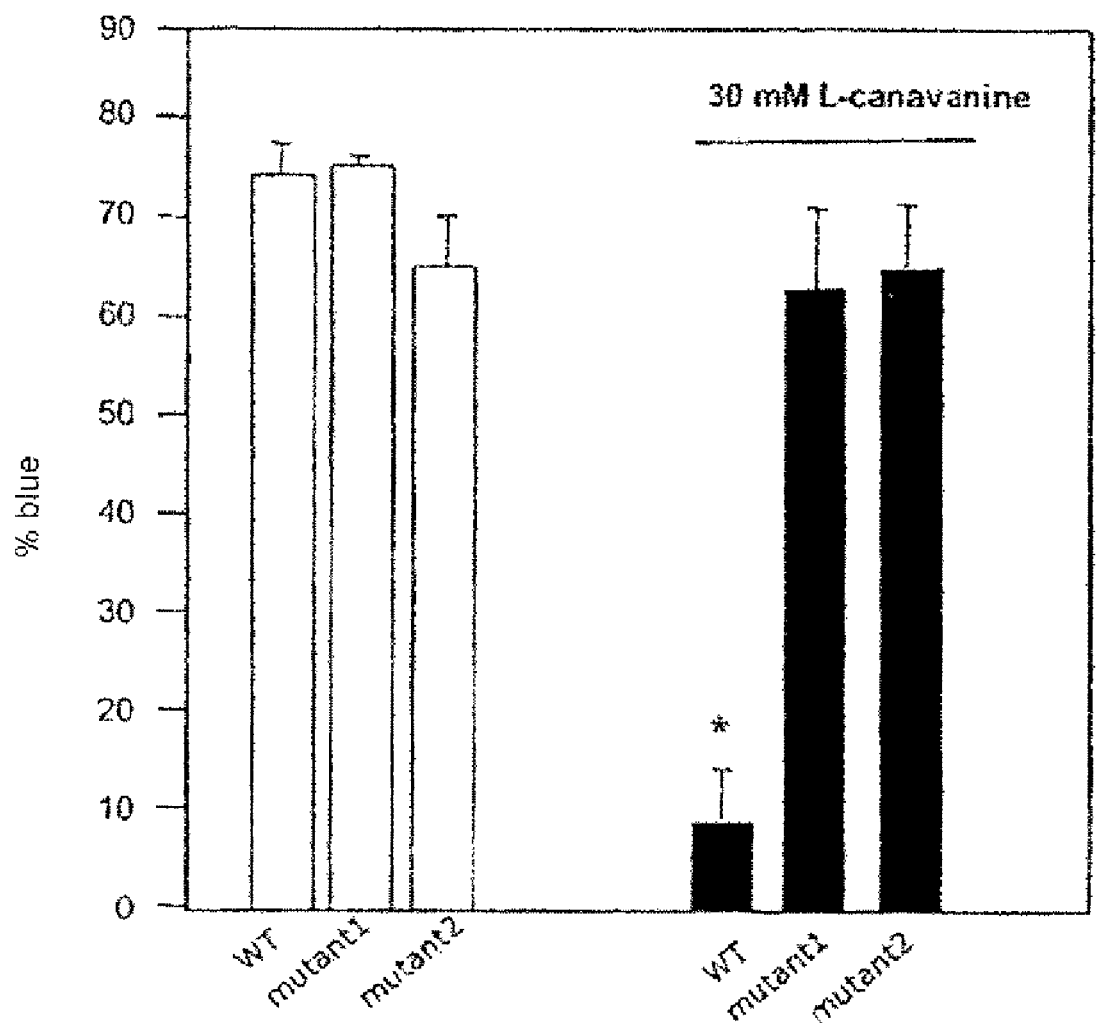

FIG. 6 gives the result of behavioral tests carried out on wild-type *drosophilas* (CS) and on two mXR function loss mutants (m1 and m2=two DmXR⁻ mutants) (n=10).

Figure 7:
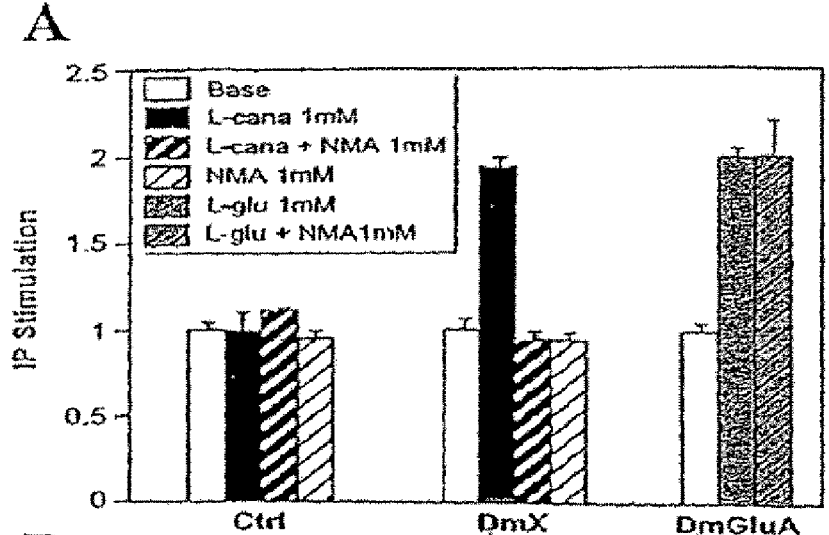
Figure 7:
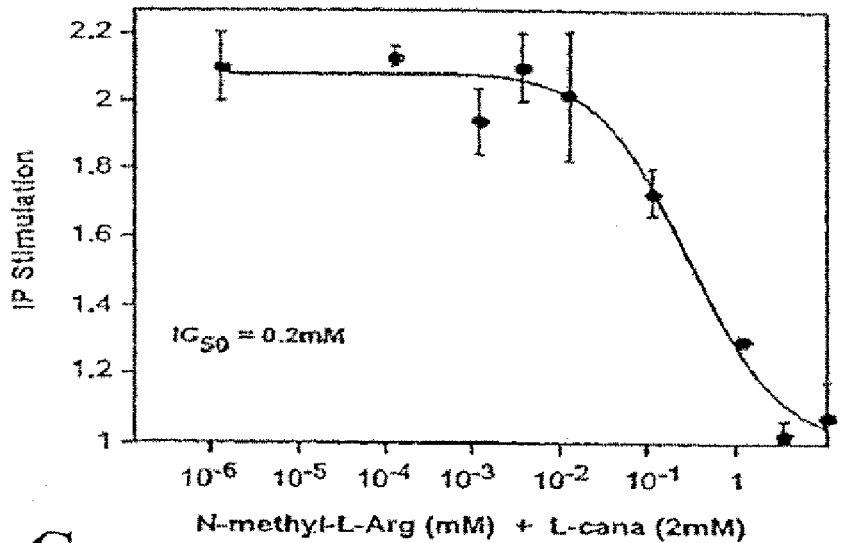
Figure 7:
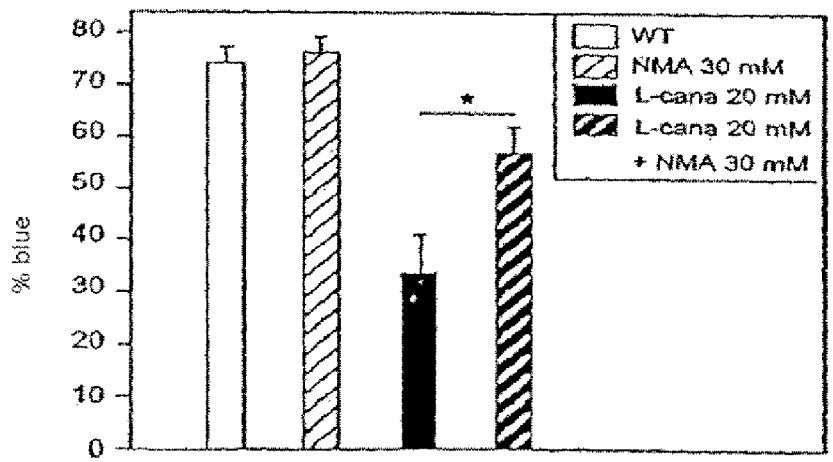

FIG. 7 shows the results obtained in vitro and in vivo with N-methyl-L-arginine. FIG. 7A shows the antagonistic effect of N-methyl-L-arginine on the DmX receptor transfected into HEK293 cells. FIG. 7B shows the N-methyl-L-arginine inhibition curve ($IC_{50}$=0.2 mM). FIG. 7C shows the result of gustatory behavior tests carried out on wild-type *drosophilas* (CS) (n=10).

Figure 8:
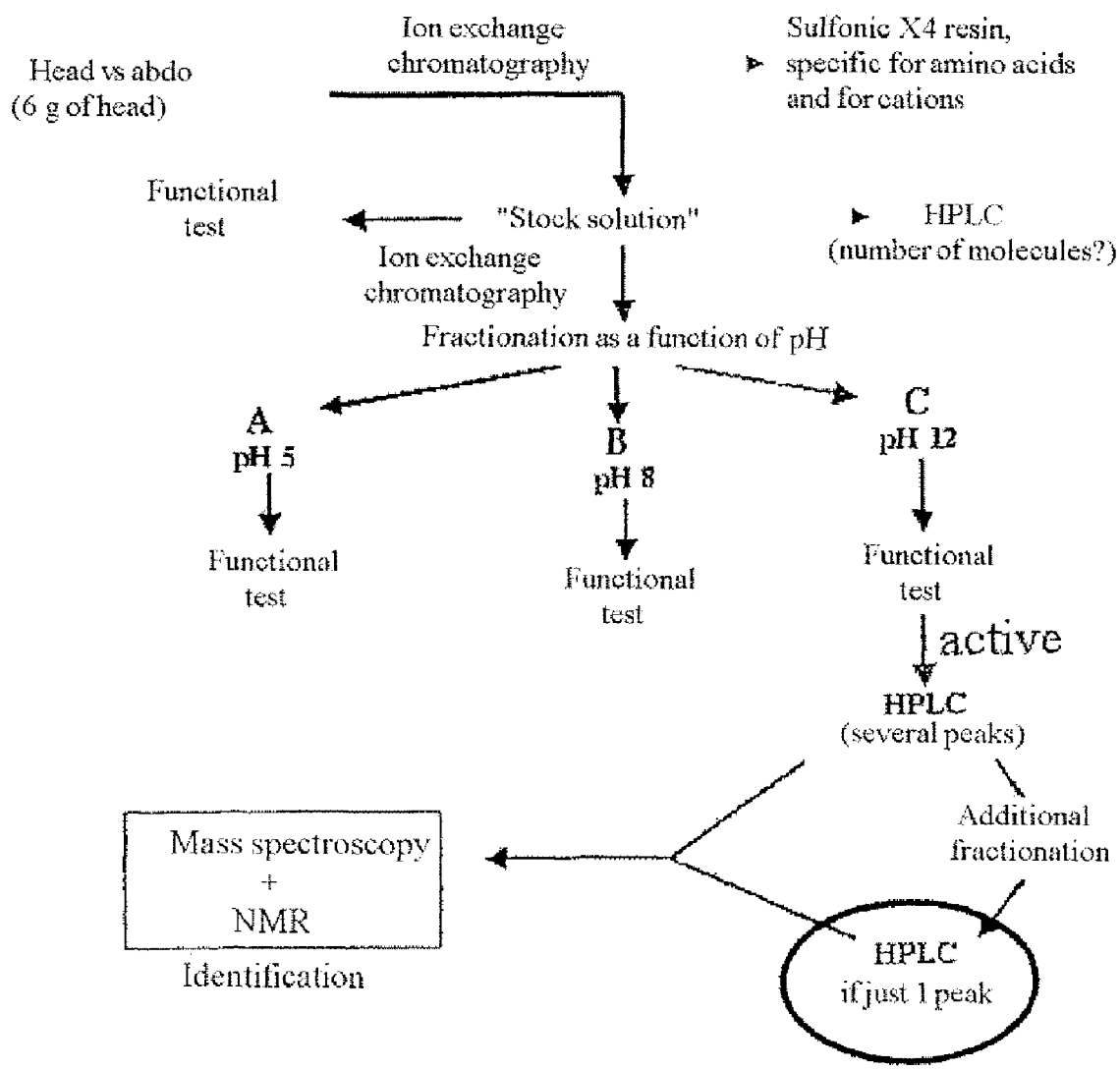

FIG. 8 illustrates the strategy used to find the endogenous ligands of DmXR.

EXAMPLES

The experimental examples described below were obtained using the following materials and methods.
Reagents The L-glutamate, L-arginine, calcium chloride, L-canavanine (ref: C1625) and N-methyl-L-arginine (ref: M-7033) were purchased from Sigma. The erioglaucine dye (ref: 861146) from Aldrich, the sulforhodamine B dye (ref: S9012) from Sigma. The agarose was purchased from Invitrogen (ref: 15510-019). The sucrose (saccharose) originates from Merck (ref: 7654).
Pharmacology The pharmacology experiments were carried out as previously described (Mitri, Parmentier et al., 2004).

For the identification of the endogenous ligand of the DmXR receptor, 6 grams of *Drosophila melanogaster*, strain Canton S, heads were used to prepare hydrophilic extracts of heads as described by Mitri et al., above. The strategy used to find the endogenous DmXR ligands is illustrated in FIG. 8. The sulfonic resin X4 comes from Biorad.
Behavior The test used measures the feeding preference in a choice with 2 possibilities materialized by two dyes, on the one hand erioglaucine (blue) and, on the other hand, sulforhodamine (red).

The erioglaucine is used at a final concentration of 5 mg/ml, dissolved in double-distilled water, pH 7.5. The sulforhodamine is used at a final concentration of 20 mg/ml, dissolved in double-distilled water, pH 7.5. The 2 dye solutions also contain sucrose fat a final concentration of 5 mM). The agonists (pH=7.5) used are added, an the final concentrations indicated on the figures, to the solution containing the erioglaucine.

To prepare a solid medium, these various compounds are added to a molten solution of agarose (0.3% final concentration, 45° C.) and deposited in a 96-well cell culture plate (*Corning Incorporated*, ref 3599) such that the wells alternately contain 200 µl of blue dye then 200 µl of red dye (see FIG. 4). The plates are left at ambient temperature for 2 hours in order for the agarose to solidify, and are then used for a feeding preference test.

For each behavioral test, 60 2- to 5-day-old *drosophilas* are deprived of food for 24 hours on cotton wool soaked with distilled water before the test and are then placed in a box containing a 96-well plate prepared as indicated above. The *drosophilas* are left in the dark for 2 hours, at 25° C., at a humidity of 30 to 50%. The *drosophilas* are then rapidly collected by anesthesia with $CO_2$ and then frozen at −20° C. for 20 minutes. In order to determine the food intake, the flies are counted according to the color of the content of their digestive tube. The results are expressed as % of flies which have eaten a given medium relative to the total number of flies which have eaten, according to the formula:

% blue=number of flies with a blue digestive tube, divided by the number of flies which have eaten (sum of the flies with a blue, violet or red digestive tube), multiplied by 100.

At least 3 independent tests were carried out for each point indicated on the figures, and the results of the tests were counted blind for the majority of the points. Only the tests in which more than 251 of the flies had eaten were included in the results and in the statistical tests (T test and ANOVA).

Genetics

The wild-type fly used is Canton S. The DmXR function loss mutants were generated by insertion of piggyBac elements (Thibault, Singer et al., 2004). The Pox-Neuro 70 mutant is available from Dr. C. Dambly-Chaudière, University of Montpellier II (Dambly-Chaudière, Jamet et al., 1992). The absence of mRNA encoding the mX receptor was shown by RT-PCR.

Example 1

In Vitro Activation of DmXR

The mX receptor is a G-protein-coupled receptor homologous to the metabotropic glutamate receptors (G-protein-coupled receptor family C) (Mitri et al., 2004). The mX receptor is characterized by a particular consensus sequence of residues in the ligand-binding pocket, which consensus sequence differs from that of the metabotropic glutamate receptors (Mitri et al., 2004).

Figure 1:
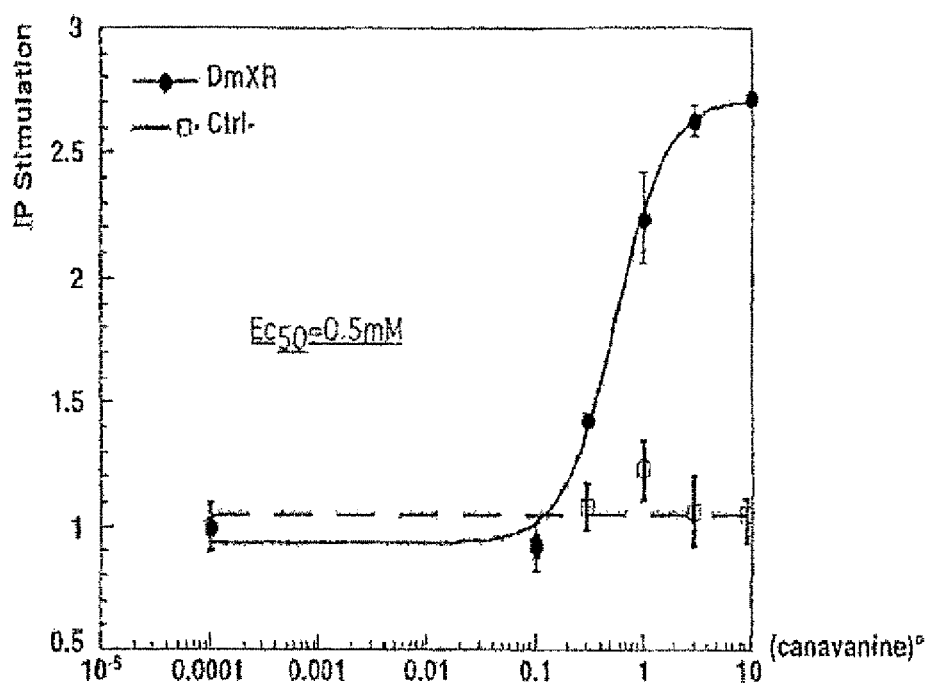
FIG. 1 shows the result of a pharmacological test showing the dose-response effect of L-canavanine on HEK cells transfected with expression vectors for Gαqi/9 alone (Ctrl), or for Gαqi/9 and DmXR (DmXR). The $EC_{50}$ of L-canavanine was evaluated at 0.5 mM.
Figure 2:
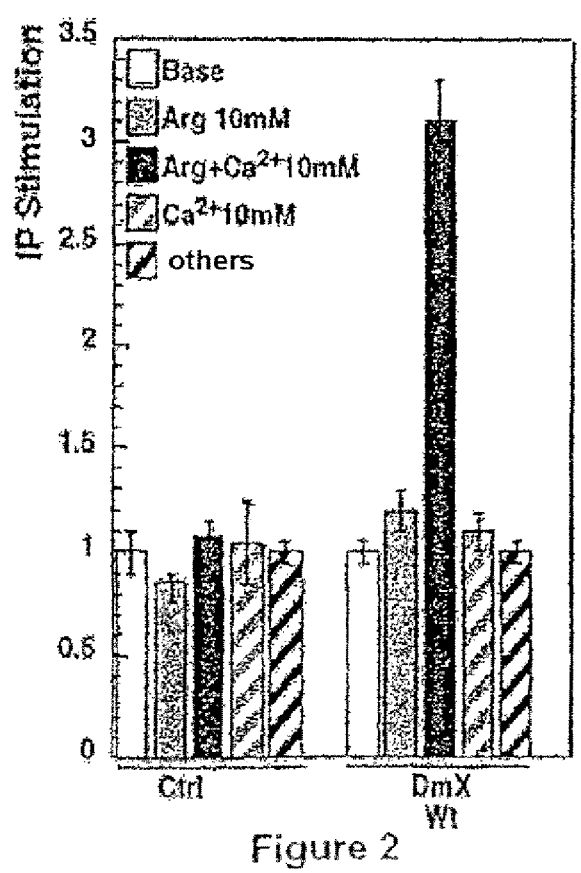
FIG. 2 shows the result of a pharmacological test showing that DmXR expressed in HEK cells is specifically activated by arginine associated with calcium, but not by the other natural amino acids (10 mM) in the presence of calcium (10 mM) (others). The "others" bar on the graph represents a mean of the tests carried out with each amino acid other than arginine.

The coding sequence of the DmX receptor was cloned into an expression vector for mammalian cells, which was then transfected into heterologous cells commonly used in pharmacology laboratories (HEK cells), as described by Mitri et al., (2004). The activation of the receptor is measured by the accumulation of inositol triphosphate. The results, given in FIGS. 1 to 3, show that:

1) in vitro, the DmX receptor is activated by L-canavanine (L-2-amino-4-(guanidmooxy)butyric acid), an amino acid with a structure analogous to arginine and synthesized by certain leguminous plants (FIG. 1). L-Canavanine is not, however, the endogenous ligand of the receptor.
2) the endogenous ligand of the DmX receptor is the amino acid L-arginine associated with the calcium ion (FIG. 2, FIG. 3).

Example 2

In Vivo Activation of DmXR

The function of the DmX receptor and the chemosensory effect of the ligands identified were studied in vivo by means of a behavioral test for measuring the food choice between two sugary solutions colored with different food dyes (erioglaucine=blue, sulfo-rhodamine=red (Thorne, Chromey et al., 2004)), in the presence or absence of the two agonists identified. FIG. 4 illustrates this behavioral test.

For each assay, 60 flies having been deprived of food (24 h) are placed in the dark on a 96-well plate for 2 h at 25° C. The wells alternately contain the test solutions in agarose (0.3%) with erioglaucine (blue) or sulforhodamine (red).

The flies are counted according to the color of the content of their digestive tube.

The results are expressed as percentage of flies which have eaten a given medium, relative to the total number of flies which have eaten.

% blue=$N$ blue/($N$ blue+$N$ violet+$N$ red)×100

The number of experiments (n) carried out is ≧8 for each situation.

In the absence of any mX receptor ligand, the flies systematically absorb more solution colored with erioglaucine (blue) than solution colored with sulforhodamine (red). This is related either to an attractant effect of the blue dye, or to a repellent effect of the red dye, or to a combination of the two effects.

The results given in FIG. 5 show that, in vivo, on the one hand L-canavanine and, on the other hand, L-arginine associated with calcium are highly repellent in a chemosensory behavioral test in *drosophila*. A sugary solution (5 mM sucrose) attracts the *drosophila*. In the presence of one of the DmXR ligands (20 mM), the sugary solution becomes repellent (FIG. 5A, FIG. 5B). At a high concentration of L-canavanine (40 mM), the sugary solution is very highly repellent (FIG. 5A).

Additional experiments show that a plateau is reached around 30 mM.

Furthermore, the tests carried out with mutant *drosophilas* (pox-neuro 70), devoid of chemosensory neurons, show that this repulsion involves the chemosensory organs of the fly (FIG. 5A).

Example 3

The Repellent Effect of L-Canavanine Requires the DmX Receptor

In order to verify that the repellent effect of L-canavanine requires the DmX receptor, the inventors identified two DmX receptor function loss mutants. For each of these mutants, m1 and m2, the absence of mRNA encoding the mX receptor was shown by RT-PCR. The results given in FIG. 6 show that these mutants have lost the ability to detect L-canavanine in the medium. In fact, the mutant *drosophilas* no longer have any repulsion with respect to L-canavanine.

These results confirm that the mX receptor activators are repellents when they are added to a sugary solution.

Example 4

Identification of New Molecules with Repellent Properties

The results given in examples 1 to 3 above make it possible to design a method for rapidly searching for new molecules with repellent properties, which uses the DmX receptor as target.

For example, such a method is made up of two phases:
1) in vitro, the cloned *drosophila* receptor (DmXR) is expressed in mammalian cells in culture. New DmX receptor modulators (agonists ligands, antagonists ligands and allosteric regulators) are identified by in vitro screening, L-canavanine serving as positive control.
2) in vivo, the DmXR activators identified in vitro are tested in *drosophila* for their repellent properties by means of a very rapid gustatory choice test, L-canavanine serving again as positive control. The repellent properties of the *drosophila* receptor activators are then tested on other insects, by means of gustatory behavior tests suitable for the species studied.

Thus, new DmXR ligands are identified, and new DmXR activators, which have a higher affinity than arginine and calcium or which are not toxic like L-canavanine, are selected.

Example 5

Identification of New Ligands by Screening In Silico

A 3D structure of the theoretical binding pocket has been determined and published (Mitri, Parmentier et al., 2004).

In order to search for new competitive ligands, a virtual screening of this 3D model of the binding site is carried out, making it possible to screen a base of more than 2 million commercial molecules.

The molecules selected virtually are then tested in vitro on the receptor. The best candidates are optimized by synthesizing various series of derivatives, the in vitro effect of which is evaluated.

The ligands identified after chemical optimization are then synthesized in sufficient amount to determine their effects in vivo.

Example 6

Identification of a DmX Receptor Inhibitor

It has been shown that the gustatory response to certain amino acids studied, such as methionine and valine, appears to depend on the insect species studied, and ranges from stimulant to repellent (Chapman 2003). The inventors therefore identified a DmX receptor antagonist, called N-methyl-L-arginine (NMA). FIG. 7A shows the antagonist effect of N-methyl-L-arginine on the DmX receptor transfected into HEK293 cells. FIG. 7B shows the N-methyl-L-arginine inhibition curve ($IC_{50}$=0.2 mM). In the gustatory behavior test used to snow the repellent effect of the DmXR agonists, NMA at a concentration of 30 mM has no effect on the gustatory behavior of *drosophila* (FIG. 7C). If NMA (30 mM) is added to the medium containing L-canavanine at a concentration of 20 mM, the repulsion is significantly less than that observed in a medium containing L-canavanine alone (FIG. 7C). This experiment confirms the repellent action of L-canavanine through the DmX receptor.

REFERENCES

Chapman, R. F. (2003). "Contact chemoreception in feeding by phytophagous insects." *Annu Rev Entomol* 48: 455-84.

Dambly-Chaudiere, C., E. Jamet, et al. (1992). "The paired box gene pox neuro: a determinant of poly-innervated sense organs in *Drosophila*." *Cell* 69(1): 159-72, Fradin, M. S. and J. F. Day (2002). "Comparative efficacy of insect repellents against mosquito bites." *N Engl J Med* 347(1): 13-8.

Gasparini, F., R. Kuhn, et al. (2002). "Allosteric modulators of group I metabotropic glutamate receptors: novel subtype-selective ligands and therapeutic perspectives." *Curr Opin Pharmacol* 2(1): 43-9.

Mitri, C, M. L. Parmentier, et al. (2004). "Divergent evolution in metabotropic glutamate receptors. A new receptor activated by an endogenous ligand different from glutamate in insects." *J Biol Chem* 279(10); 9313-20.

Rosenthal, G. A. (1977), "The biological effects and mode of action of L-canavanine, a structural analogue of L-arginine." *Q Rev Biol* 52(2): 155-79.

Rosenthal, G. A. (2001). "L-Canavanine: a higher plant insecticidal allelochemical." *Amino Acids* 21(3): 319-30.

Thibault, S. T., M. A. Singer, et al. (2004). "A complementary transposon tool kit for *Drosophila melanogaster* using P and piggyBac." *Nat Genet* 36(3): 283-7.

Thorne, N., C. Chromey, et al. (2004). "Taste perception and coding in *Drosophila*." *Curr Biol* 14(12): 1065-79.

The invention claimed is:

1. A screening method for identifying a substance that is a repellent for at least one insect species, comprising identifying a substance that-binds to an mX receptor of said insect.

2. The method as claimed in claim 1, further comprising identifying a substance that activates the mX receptor.

3. The method as claimed in claim 1, wherein the mX receptor is selected from the group consisting of the DmXR receptor of *Drosophila melanogaster, Drosophila pseudoobscura* or *Drosophila virilis*, the AgmXR receptor of *Anopheles gambiae*, the mXR receptor of *Aedes aegyti*, the HBmXR receptor of *Apis mellifera* and the mXR receptor of *Bombyx mori*.

4. The method as claimed in claim 1, comprising bringing the substance into contact with the mX receptor in vitro.

5. The method as claimed in claim 4, wherein the in vitro screening is carried out on cells in culture which express the mX receptor.

6. The method as claimed in claim 1, further comprising-determining, in vivo, the repellent effect of the substance identified in vitro.

7. The method as claimed in claim 6, wherein the step of determining, in vivo, the repellent effect comprises a gustatory choice test.

8. The method as claimed in claim 1, further comprising screening the substance in silico before screening the substance in vitro.

9. The method of claim 1, further comprising testing at least one mX receptor function loss mutant in order to determine whether the repellent action of the substance identified is exclusively linked to the binding of said substance to the mX receptor.

* * * * *